United States Patent [19]
Elmore

[11] Patent Number: 5,623,025
[45] Date of Patent: Apr. 22, 1997

[54] EPOXY-FUNCTIONAL HYDROXY ESTERS

[75] Inventor: Jimmy D. Elmore, Houston, Tex.

[73] Assignee: Shell Oil Company, Houston, Tex.

[21] Appl. No.: 643,196

[22] Filed: May 6, 1996

Related U.S. Application Data

[63] Continuation of Ser. No. 361,075, Dec. 21, 1994, abandoned.

[51] Int. Cl.⁶ ........................................................ C08F 4/42
[52] U.S. Cl. ............................ 525/450; 525/488; 525/533
[58] Field of Search .................................... 525/450, 488, 525/533; 528/365

[56] References Cited

U.S. PATENT DOCUMENTS 5,118,729  6/1992  Piechocki ............................... 523/404
5,250,727  10/1993  Fried ........................................ 562/540

*Primary Examiner*—Paul R. Michl
*Assistant Examiner*—U. K. Rajguru

[57] ABSTRACT

A novel epoxy-functional hydroxy ester composition is produced by reacting (a) dimethylolpropionic acid and (b) an aliphatic or cycloaliphatic glycidyl ether, an epoxy novolac or a cycloaliphatic epoxy having a functionality of at least about 1.5 epoxide group per molecule.

20 Claims, No Drawings

EPOXY-FUNCTIONAL HYDROXY ESTERS

This is a continuation of application Ser. No. 08/361,075, now abandoned, filed Dec. 21, 1994.

FIELD OF INVENTION

This invention relates to epoxy-functional hydroxy esters. In one aspect, the invention relates to a process to produce epoxy-functional hydroxy esters and the epoxy-functional hydroxy esters produced therefrom.

BACKGROUND OF THE INVENTION

There are ever increasing demands for compounds useful in epoxy resin applications, for example as emulsifiers or diluents, as epoxy resins are required to perform under ever more specific and demanding conditions. For epoxy resin applications it is desirable for such a compound to have epoxy functional groups to increase the compatibility with the cured epoxy matrix. Further, it is desirable to be able to provide compounds with predefined hydrophilic and hydrophobic segments depending on the desired applications. Therefore it is desirable to provide a novel process that can control the hydrophilic and hydrophobic properties of the compounds.

It is therefore an object of the present invention to provide novel epoxy-functional hydroxy esters. It is another object of the present invention to provide a novel process to prepare epoxy-functional hydroxy esters.

SUMMARY OF THE INVENTION

According to the invention, an epoxy ether hydroxy ester is provided as exemplified by the formula:

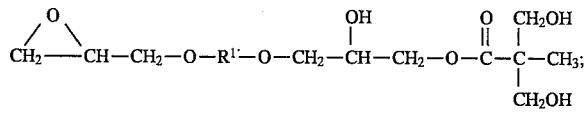  (I)

wherein $R^1$ is an alkylene, oxyalkylene, or a cycloalkylene group, $R^2$ is independently a hydrogen or a $C_1$–$C_{10}$ alkyl group, $R^4$ is a divalent aliphatic group optionally containing ether or ester group(s) or together with $R^7$ or $R^8$ form a spiro ring optionally containing heteroatoms, and $R^7$ and $R^8$ are independently hydrogen or $R^7$ or $R^8$ together form a spiro ring optionally containing heteroatoms such as oxygen, and r is a real number from about 0 to about 6.

The epoxy-functional hydroxy ester composition is produced by reacting (a) dimethylolpropionic acid and (b) an aliphatic or cycloaliphatic glycidyl ether, an epoxy novolac or a cycloaliphatic epoxy having a functionality of at least about 1.5 epoxide group per molecule.

DETAILED DESCRIPTION OF THE INVENTION

The epoxy-functional hydroxy ester of the invention is produced by reacting dimethylolpropionic acid and an hydrophobic epoxy resin such as aliphatic or cycloaliphatic glycidyl ethers, epoxy novolacs or cycloaliphatic epoxies having a functionality (1,2-epoxy equivalency) preferably, on the average, of at least about 1.5 epoxide groups per molecule in a dimethylol propionic acid to epoxy resin mole ratio of from about 1:1, preferably from about 1:1.3 to about 1:500, preferably to about 1:200.

The aliphatic or cycloaliphatic epoxy resin can be saturated or unsaturated, linear or branched and may bear substituents which do not materially interfere with the reaction with the dimethylolpropionic acid. Such substituents can include bromine or fluorine. They may be monomeric or polymeric, liquid or solid, but are preferably liquid or a low melting solid at room temperature. Suitable epoxy resins include glycidyl ethers prepared by reacting epichlo-

 (II)

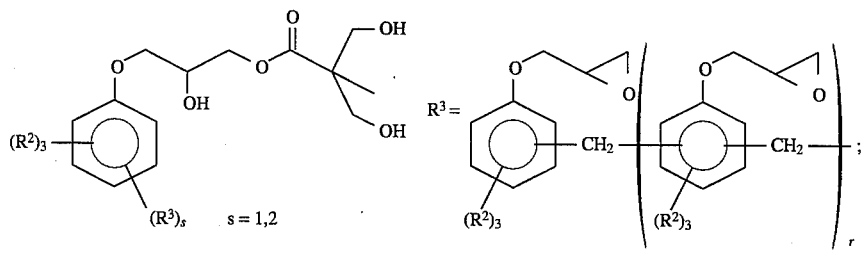

 (III)

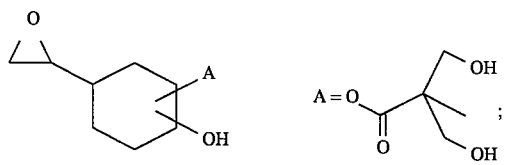

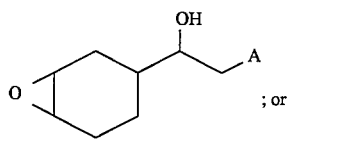

 (IV)

; or

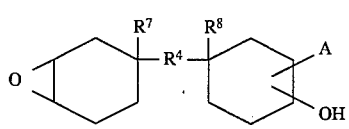 (V)

rohydrin with a compound containing a real positive number of at least 1.5 hydroxyl group carried out under alkaline reaction conditions. Examples of epoxy resins suitable for use in the invention include diglycidyl ethers of aliphatic or cycloaliphatic dihydric compounds. Aliphatic as used herein can be saturated or unsaturated, linear or branched alkylene groups. Cycloaliphatic as used herein can be any aliphatic group containing cyclic moiety. The term aliphatic or cycloaliphatic includes compounds having oxygen and/or sulfur atoms on the backbone. Generally epoxy resins contain a distribution of compounds with a varying number of 1,2-epoxy equivalency.

Preferred epoxy resin include, but not limited to, those represented by the formula:

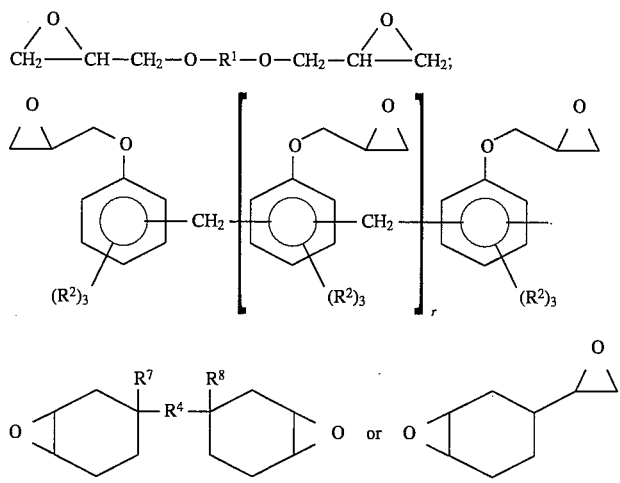

wherein $R^1$ is a divalent alkene, divalent oxyalkylene, or a divalent cycloalkylene group, preferably $R^1$ contains about 2 to 20 carbon atoms, $R^2$ is independently a hydrogen or a $C_1$–$C_{10}$ alkyl group, $R^4$ is a divalent aliphatic group optionally containing ether or ester group(s) or together with $R^7$ or $R^8$ form a spiro ring optionally containing heteroatoms, and, $R^7$ and $R^8$ are independently hydrogen or $R^7$ or $R^8$ together form a spiro ring optionally containing heteroatoms such as oxygen, and r is a real number from about 0 to about 6.

Preferably the epoxy resin is an aliphatic or cycloaliphatic glycidyl ether, epoxy novolac or a cycloaliphatic epoxy.

Cycloaliphatic glycidyl ethers (or diglycidyl ethers of hydrogenated dihydric phenols) can be produced, for example, by hydrogenation of dihydric phenols followed by glycidation with epihalohydrin in the presence of a lewis catalyst and subsequent formation of the glycidyl ether by reaction with sodium hydroxide. Examples of suitable dihydric phenols include: 2,2-bis(4-hydroxyphenyl) propane (bisphenol-A); 2,2-bis(4-hydroxy-3-tert-butylphenyl) propane; 1,1-bis(4-hydroxyphenyl) ethane; 1,1-bis(4-hydroxyphenyl) isobutane; bis(2-hydroxy-1-naphthyl) methane; 1,5-dihydroxynaphthalene; 1,1-bis(4-hydroxy-3-alkylphenyl) ethane and the like. Suitable dihydric phenols can also be obtained from the reaction of phenol with aldehydes such as formaldehyde (bisphenol-F).

Examples of preferred cycloaliphatic epoxy resin include those corresponding to the formulas:

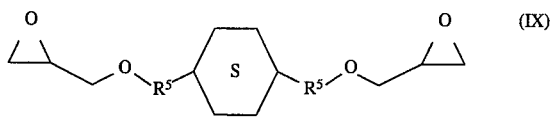

(IX)

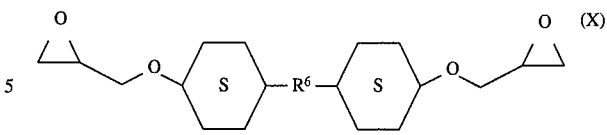

(X)

wherein independently $R^5$ and $R^6$ are an alkylene group. Preferably $R^5$ is methylene and $R^6$ is $C_{1-12}$ alkylene group.

Aliphatic glycidyl ethers can be produced, for example, by reacting an epihalohydrin with an aliphatic diol (optional containing ether linkages or sulfone linkages) in the presence of a Lewis acid catalyst followed by conversion of the halohydrin intermediate to the glycidyl ether by reaction with sodium hydroxide.

(VI)

(VII)

(VIII)

Examples of preferred aliphatic glycidyl ethers include those corresponding to the formulas:

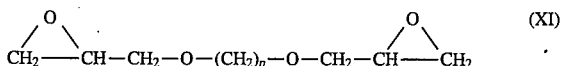

(XI)

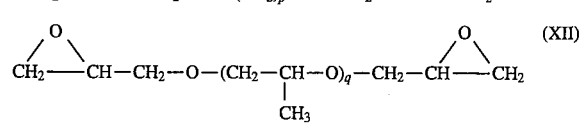

(XII)

wherein:

p is an integer from 2 to 12, preferably from 2 to 6; and q is an integer from 4 to 24, preferably from 4 to 12.

Examples of suitable aliphatic glycidyl ethers include for example, diglycidyl ethers of 1,4 butanediol, neopentyl glycol, cyclohexane dimethanol, hexanediol, polyproplene glycol, and polyglycol; and triglycidyl ethers of trimethylol ethane and trimethylol propane.

Epoxy novolacs can be produced by condensation of formaldehyde and a phenol followed by glycidation by epihalohydrin in the presence of an alkali. The phenol can be for example, phenol, cresol, nonylphenol and t-butylphenol.

Examples of the preferred epoxy novolacs include those corresponding to the formula:

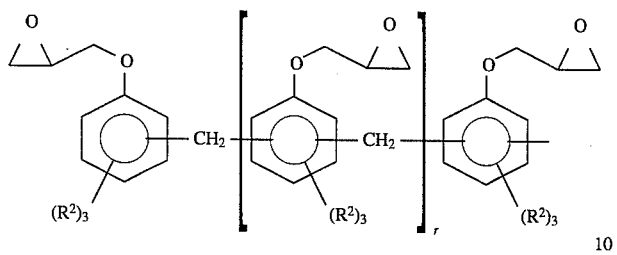

wherein $R^2$ is independently a hydrogen or a $C_1$–$C_{10}$ alkyl group and r is a real number from about 0 to about 6. Epoxy novolacs generally contain a distribution of compounds with a varying number of glycidated phenoxymethylene units, r.

Cycloaliphatic epoxies can be produced by epoxidizing a cycloalkene-containing compound with greater then one olefinic bond with peracetic acid. Examples of the preferred cycloaliphatic epoxies include those corresponding to the formula:

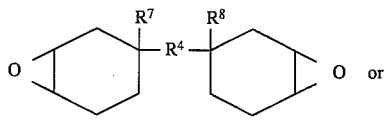

(VIII)

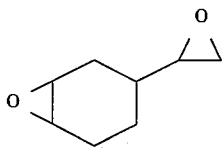

wherein $R^4$ is a divalent aliphatic group optionally containing ether or ester group(s) or together with $R^7$ or $R^8$ form a spiro ring optionally containing heteroatoms, and, $R^7$ and $R^8$ are independently hydrogen or $R^7$ or $R^8$ together form a spiro ring optionally containing heteroatoms such as oxygen, preferably $R^4$ contains about 1 to 20 carbon atoms. Examples of cycloaliphatic epoxies include, for example, 3,4-epoxycyclohexylmethyl-(3,4-epoxy)cyclohexane carboxylate, dicycloaliphatic diether diepoxy [2-(3,4-epoxy-)cyclohexyl-5,5-spiro(3,4-epoxy)-cyclohexane-m-dioxane], bis(3,4-epoxycyclohexylmethyl)adipate, bis(3,4-epoxycyclohexyl)adipate and vinylcyclohexene dioxide [4-(1,2-epoxyethyl)-1,2-epoxycyclohexane].

Commercial examples of preferred epoxy resins include, for example, EPONEX® Resin 1510, HELOXY® Modifiers 107, 67, 68, and 32 all available from Shell Chemical Company and Union Carbide Epoxy Resin ERL-4221, -4289, -4299, -4234 and -4206.

The dimethylolpropionic acid is contacted with the epoxy resin under conditions effective to react the acid group and the epoxide group and to produce epoxy-functional hydroxy esters represented by the formulas:

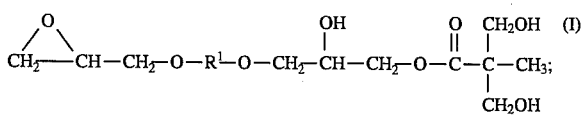

(I)

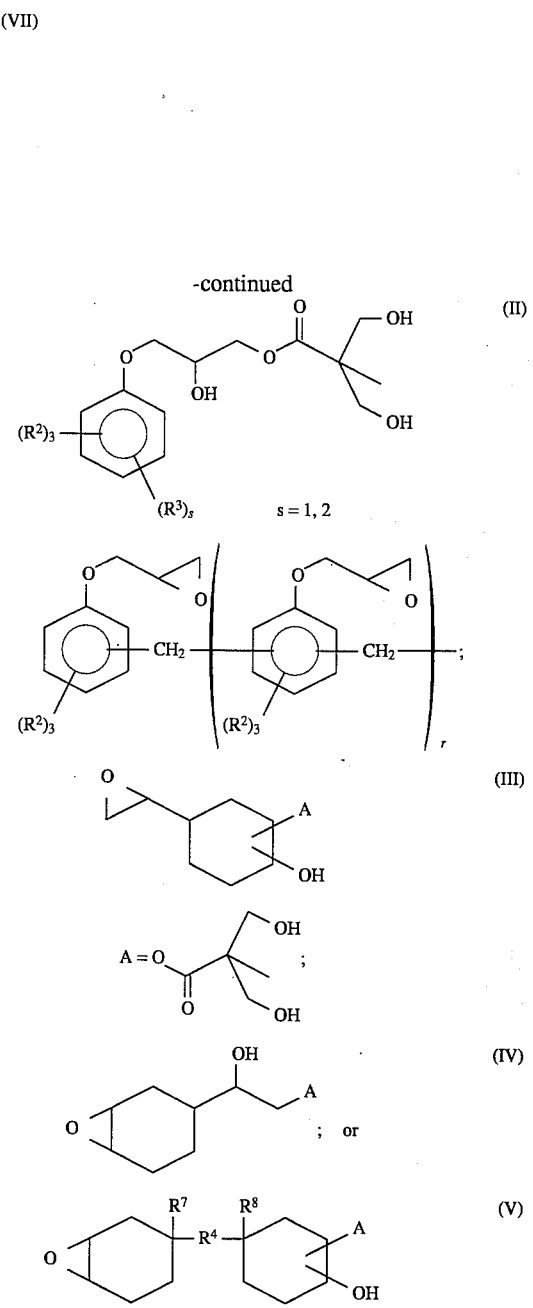

wherein $R^1$ is an alkylene, oxyalkylene, or a cycloalkylene group preferably having from 2 to 20 carbon atoms, $R^2$ is independently a hydrogen or a $C_1$–$C_{10}$ alkyl group, $R^4$ is a divalent aliphatic group optionally containing ether or ester group(s) or together with $R^7$ or $R^8$ form a spiro ring optionally containing heteroatoms, and $R^7$ and $R^8$ are independently hydrogen or $R^7$ or $R^8$ together form a spiro ring optionally containing heteroatoms such as oxygen, and r is a real number from about 0 to about 6. The location of the OH and A bonding to the cycloaliphatic ring represents the different isomers formed by the cycloaliphatic ring opening reaction. It can be appreciated that the acid A moiety can be attached to either para- or metal- position from $R^4$ or epoxy moiety.

Typically, the mole ratio of the dimethylolpropionic acid to epoxy resin is within the range of about 1:1 to about 1:500, more preferably from about 1:1.3 to about 1:200. The reaction is typically carried out at a temperature from ambient temperature to an elevated temperature sufficient to react the acid group and the epoxide group which is typically within the range of from about 25° C., preferably from about 90° C., to about 150° C., preferably to about 120° C. for a time effective to produce the reaction products. The progress of the reaction can be monitored and targeted to produce the desired product by measuring the acid equivalent weight and the epoxy epoxy equivalent weight of the reactant mixture. Generally, the reaction mixture is heated until an acid equivalent weight of the mixture indicates that greater or equal than 99% of the original number of equivalents of acid is consumed, and at least an equivalent amount of epoxies is consumed which is generally one hour or greater. For cycloaliphatic epoxies, the monitoring of the course of reaction by following consumption of epoxy alone can be misleading, due to competing homopolymerization of this type of epoxy group. Preferably, this reaction is carried out in the presence of an catalyst.

The reaction typically produces a product which contains at least one epoxide monoester and molecules which result from the condensation of two or more molecules of acid with one molecules of polyepoxide as well as unreacted epoxide depending on the mole or equivalent ratios of the epoxy resin to the carboxylic acid groups and the amount of time the reaction is allowed to proceed. Preferably, excess of the epoxy resin (mole ratio of the epoxy resin to carboxylic acid being greater than about 1:1) is used to minimize the formation of the polyesterified species. If desired the epoxide monoester product of a mixture containing predominantly epoxide monoester product (monoester being the largest component in the mixture) can be recovered from the reaction mixture by conventional techniques.

The catalysts are bases or metal chelates such as, for example, ammonium compounds, phosphonium compounds, tertiary amines, and phosphines. Examples of more preferred catalysts include, for example, triphenylphosphonium acid acetate, ethyltriphenyl phosphonium iodide, benzyldimethylamine, triphenylphosphine, tributylamine, aluminum salicylates, tetramethylammonium hydroxide and the like. The amount of catalyst present is preferably from about 0.05, more preferably from about 0.01, to about 2.0, more preferably to about 0.5 weight percent based on the total weight of the epoxy resin and the carboxylic acid.

Illustrative Embodiment

The following illustrative embodiments describe the process of the invention and are provided for illustrative purposes and are not meant as limiting the invention.

Examples 1 demonstrate the preparation of the epoxy-functional hydroxy esters of the invention.

HELOXY® Modifier 67 (a diglycidyl ether of butanediol having an epoxy equivalent weight of 333) was obtained from Shell Chemical Company. 25% active aluminum salicylate was obtained from Rhone Poulenc Marichem Inc.

EXAMPLE 1

An epoxy-functional hydroxy ester having the following formula was prepared.

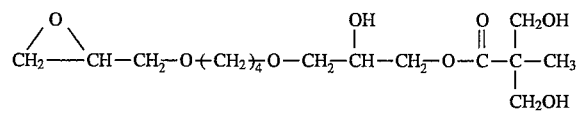

Batch Procedure: 2,768.5 grams of HELOXY® 67 and 254.0 grams of 2,2 hydroxymethyl propanoic acid (DMPA) were added to an appropriate three neck, round bottom flask fitted with a mechanical agitator. To this batch was added 2.73 grams of ethyl triphenyl phosphonium acid acetate and 7.71 grams of a 25% aluminum salicylate solution (catalysts). This batch was heated to 195° F. with mixing and held at this temperature for 142 minutes. A second addition, equal to the first amounts of DMPA and catalysts, was then added and the batch was held at 194° F. for an additional 165 minutes. Then a third addition, equal to the first amounts of DMPA and catalysts, was added and the batch was held at 194° F. for 255 minutes. Then the fourth addition, equal to the first amounts of DMPA and catalysts, was made and the batch was held at 195° F. for an additional 5 hours. The batch was allowed to cool to room temperature.

We claim:

1. A composition comprising a product produced by reacting dimethylolpropionic acid and an epoxy resin selected from the group consisting of aliphatic or cycloaliphatic glycidyl ethers, epoxy novolacs and cycloaliphatic epoxies, said epoxy resin having a functionality of at least about 1.5 epoxide group per molecule in a dimethylol propionic acid to epoxy resin mole ratio of from about 1:1 to about 1:500.

2. The composition of claim 1 wherein the epoxy resin has the formula:

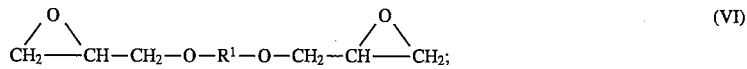 (VI)

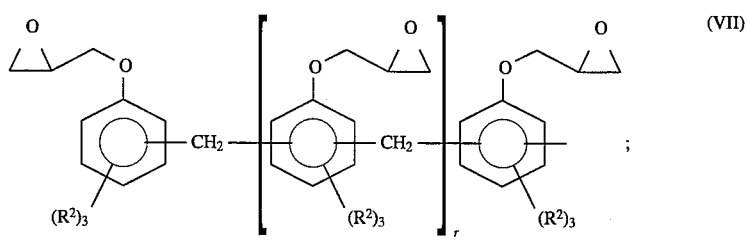 (VII)

or

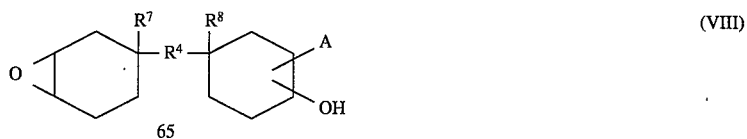 (VIII)

wherein $R^1$ is a divalent alkene, divalent oxyalkylene, or a divalent cycloalkylene group, $R^2$ is independently a hydrogen or a $C_1$–$C_{10}$ alkyl group, $R^4$ is a divalent aliphatic group optionally containing ether or ester group(s) or together with $R^7$ or $R^8$ form a spiro ring optionally containing heteroatoms, and, $R^7$ and $R^8$ are independently hydrogen or $R^7$ or $R^8$ together form a spiro ring optionally containing heteroatoms such as oxygen, and r is a real number from about 0 to about 6.

3. The composition of claim 1 wherein the product is produced by reacting dimethylol propionic acid and a cycloaliphatic glycidyl ether.

4. The composition of claim 1 wherein the product is produced by reacting dimethylol propionic acid and an aliphatic glycidyl ether.

5. The composition of claim 1 wherein the product is produced by reacting dimethylol propionic acid and an epoxy novolac.

6. The composition of claim 1 wherein the product is produced by reacting dimethylol propionic acid and a cycloaliphatic epoxy.

7. The composition of claim 4 wherein the aliphatic glycidyl ether have the formula:

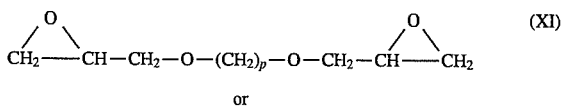

or

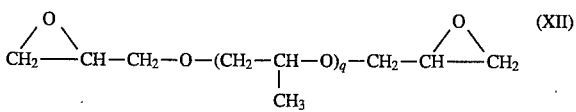

wherein:

p is an integer from 2 to 12; and q is an integer from 4 to 24.

8. The composition of claim 7 wherein the aliphatic epoxy resin is selected from the group consisting of diglycidylether of 1,4 butanediol, neopentyl glycol, cyclohexane dimethanol, hexanediol, polyproplene glycol, and polyglycol; and triglycidyl ethers of trimethylol ethane and trimethylol propane.

9. A composition comprising a compound having the formula:

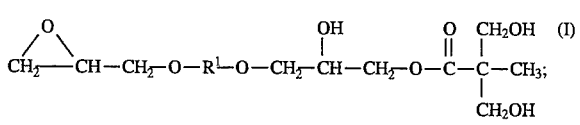

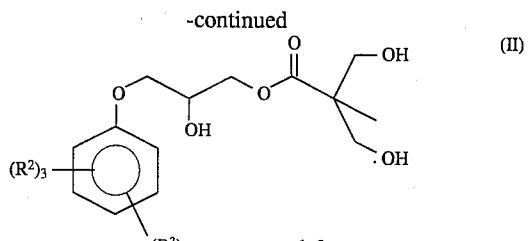

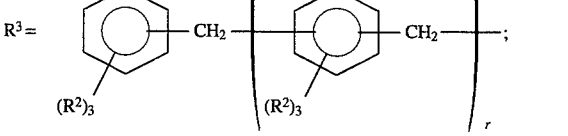

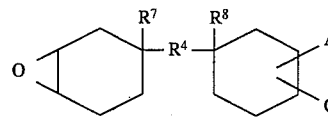

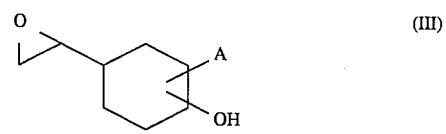

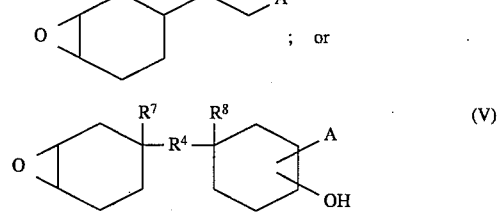

wherein $R^1$ is an alkylene, an oxyalkylene, or a cycloalkylene group, $R^2$ is independently a hydrogen or a $C_1$–$C_{10}$ alkyl group, $R^4$ is a divalent aliphatic group optionally containing ether or ester group(s) or together with $R^7$ or $R^8$ form a spiro ring optionally containing heteroatoms, and $R^7$ and $R^8$ are independently hydrogen or $R^7$ or $R^8$ together form a spiro ring optionally containing heteroatoms such as oxygen, and r is a real number from about 0 to about 6.

10. A composition comprising a compound having the formula:

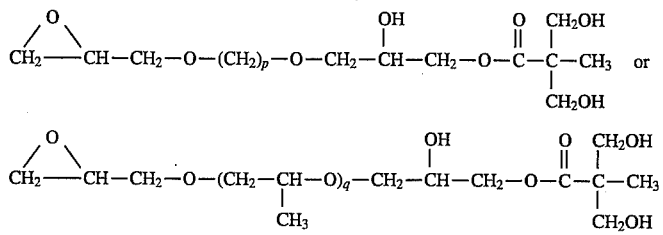

wherein:

p is an integer from 2 to 12; and q is an integer from 4 to 24.

11. A method for producing an epoxyether hydroxyester comprising reacting dimethylolpropionic acid and an epoxy resin selected from the group consisting of aliphatic or cycloaliphatic glycidyl ethers, epoxy novolacs, and cycloaliphatic epoxies, said epoxy resin having a functionality of at least about 1.5 epoxide group per molecule in a dimethylolpropionic acid to epoxy resin mole ratio of from about 1:1 to about 1:500 under conditions effective to react the acid group and the epoxy group.

12. The method of claim 11 wherein the dimethylolpropionic acid and the epoxy resin are reacted at a temperature within the range of about 25° C. to about 150° C.

13. The method of claim 12 wherein the dimethylolpropionic acid and the epoxy resin are reacted in the presence of a base or a metal chelate.

14. The method of claim 13 wherein the dimethylolpropionic acid and the epoxy resin are reacted in the presence of a catalyst selected from the group consisting of ammonium compounds, phosphonium compounds, tertiary amines, and phosphines.

15. The composition of claim 1 wherein the epoxy resin is selected from the group consisting of diglycidylether of 1,4 butanediol, neopentyl glycol, cyclohexane dimethanol, hexanediol and polypropylene glycol.

16. The composition of claim 10 wherein the compound has a formula:

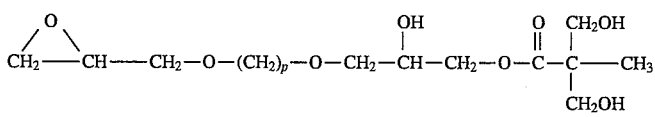

wherein:

p is an integer from 2 to 6.

17. The composition of claim 16 wherein p is an integer of 4.

18. The method of claim 13 wherein the epoxy resin is an aliphatic glycidyl ether.

19. The method of claim 18 wherein the aliphatic glycidyl ether have the formula:

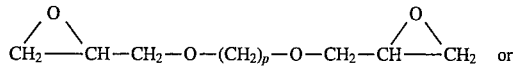 (XI)

or

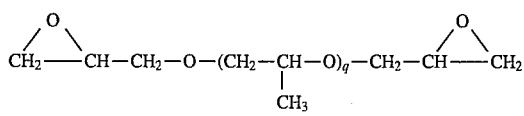 (XII)

wherein:

p is an integer from 2 to 12; and q is an integer from 4 to 24.

20. The method of claim 18 wherein the epoxy resin is selected from the group consisting of diglycidylether of 1,4 butanediol, neopentyl glycol, cyclohexane dimethanol, hexanediol and polypropylene glycol.

* * * * *